United States Patent
Chaturvedi et al.

(10) Patent No.: US 6,824,769 B2
(45) Date of Patent: Nov. 30, 2004

(54) OPTIMAL COMPOSITIONS AND METHODS THEREOF FOR TREATING HCV INFECTIONS

(75) Inventors: Pravin Chaturvedi, Andover, MA (US); Ene Ette, Framingham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/941,282

(22) Filed: Aug. 28, 2001

(65) Prior Publication Data

US 2003/0068302 A1 Apr. 10, 2003

(51) Int. Cl.⁷ .................. A61K 38/21; A61K 38/00; A61K 31/17; C07K 17/00
(52) U.S. Cl. .................. 424/85.7; 514/2; 514/588; 424/85.4; 530/351
(58) Field of Search .................. 517/2; 424/85.9, 424/85.7; 530/351; 514/588

(56) References Cited

PUBLICATIONS

Wright et al., 1999, Hepatology vol. 30, No. 4, pt. 2, p. 408A.*
Markland et al., 2000, Antimicrobial Agents and Chemotherapy, vol. 44, pp. 859–866.*
Paul Glue, M.D., Ph.D., "The Clinical Pharmacology of Ribavirin", Seminars in Liver Disease, vol. 19, 17–24, Supplment 1, 1999.
Khakoo et al., "Ribavirn and Interfero Alfa–2b in Chronic Hepatitis C: Assessment of Possible Pharmacokinetic and Pharmacodynamic Interactions", Br. J. Clin Pharmacol, 46: 563–570, 1998.
Brunet et al., "Pharmacokinetics and Pharmacodynaics of Mycophenolic Acid in Stable Renal Transplant Recipients Treated with Low Doses of Mycophenolate Mofetil", Transpl. Int. 13 [Suppl 1] S301–S305, 2000.
McHutchinson et al., "Combination Therapy With Interferon Plus Ribavirin for the Initial Treatment of Chronic Hepatitis C", Seminars in Liver Disease, 19: [Suppl. 1] 57–65, 1999.

* cited by examiner

Primary Examiner—Janet Andres
(74) Attorney, Agent, or Firm—Michael C. Badia; Vertex Pharmaceuticals Incorporated

(57) ABSTRACT

The present invention relates to optimal compositions useful in treating HCV infections in humans. These compositions comprise alpha-interferon or a derivative thereof and an IMPDH inhibitor, wherein the IMPDH inhibitor is present in an amount such that a ratio of Cavg/Cmin is between 1 to 10, wherein:

Cavg is average plasma concentration produced by said IMPDH inhibitor in said human; and Cmin is estimated trough concentration produced by said IMPDH inhibitor in said human.

The present invention also relates to methods of producing and using the optimal compositions to treat HCV infections in humans.

7 Claims, No Drawings

US 6,824,769 B2

OPTIMAL COMPOSITIONS AND METHODS THEREOF FOR TREATING HCV INFECTIONS

TECHNICAL FIELD OF THE INVENTION

The present invention relates to optimal compositions useful in treating HCV infections in humans. These compositions comprise alpha-interferon and an IMPDH inhibitor, wherein the IMPDH inhibitor is present in an amount such that a ratio of Cavg/Cmin is between 1 to 10, wherein:

Cavg is average plasma concentration produced by said IMPDH inhibitor in said human; and Cmin is estimated trough concentration produced by said IMPDH inhibitor in said human.

The present invention also relates to methods of producing and using the optimal compositions to treat HCV infections in humans.

BACKGROUND OF THE INVENTION

Hepatitis C virus ("HCV") infection is a common cause of viral hepatitis. It is estimated that 3% of the world's population is infected with HCV. (Clarke, B. E., *Balliere's Clinical Gastroenterology,* 14, No. 2, pp. 293–305 (2000). Until recently, alpha-interferon was the first therapy with proven benefit for treating HCV infection. Depletion of cellular guanine nucleotide reservoirs via inhibition of the NAD+-dependent enzyme, inosine monophosphate dehydrogenase ("IMPDH"), which is the rate-limiting enzyme in the de novo nucleotide biosynthesis, has been identified as an attractive target for anti-HCV therapy. See, VX-497, *Drugs of the Future,* 25(8), pp. 809–814 (2000). Known inhibitors of IMPDH include Ribavirin, VX-497, mycophenolate mofetil (Cellcept™), tiazofurin and mizoribine. Recently, a combination therapy, using alpha-interferon and Ribavirin™, has shown greater efficacy in treating HCV infection than a monotherapy using either entity. However, the combination therapy is not problem free. Alpha interferon is known to cause side effects such as high fevers, headaches, nausea and depression. Ribavirin tends to increase these side effects, and also cause haemolytic anaemia. Hepatologists are reluctant to reduce the dosage of Ribavirin below 800 mg/day (see, Foster, G. R. and Thomas, H. C., *Balliere's Clinical Gastroenterology,* 14(2), pp. 255–264 (2000). The minimum effective dose of Ribavirin is not yet known.

Thus, there is a need for a therapy that takes advantage of the synergy and/or additivity observed between alpha-interferon and an IMPDH inhibitor in the combination therapy, but preferably without the drawbacks associated with the individual components of the combination therapy.

Thus, there is a need for an optimal composition for treating HCV infection in a human, comprising alpha-interferon and an IMPDH inhibitor.

There is also a need for a method for treating HCV infection in a human comprising the step of administering to said human an optimal composition comprising alpha-interferon and an IMPDH inhibitor.

There is also a need for a method for evaluating the suitability of a composition comprising an IMPDH inhibitor and alpha-interferon for optimally treating HCV infection in a human.

There is also a need for a method of producing an optimal composition for treating HCV infection in a human, wherein said optimal composition comprises alpha-interferon and an IMPDH inhibitor.

SUMMARY OF THE INVENTION

It is an object of the present invention to provide an optimal composition for treating HCV infection in a human, comprising alpha-interferon and an IMPDH inhibitor, wherein said IMPDH inhibitor is present in said composition in an amount such that a ratio of Cavg/Cmin is between 1 to 10;

wherein:

Cavg is average plasma concentration produced by said IMPDH inhibitor in said human; and Cmin is estimated trough concentration produced by said IMPDH inhibitor in said human.

It is another object of the present invention to provide a method for treating HCV infection in a human comprising the step of administering to said human an optimal composition comprising alpha-interferon and an IMPDH inhibitor, wherein said optimal composition contains said IMPDH inhibitor in an amount such that a ratio of Cavg/Cmin is between 1to 10;

wherein Cavg and Cmin are as described above.

It is yet another object of the present invention to provide a method for evaluating the suitability of a composition comprising an IMPDH inhibitor and alpha-interferon for treating HCV infection in a human, said method comprising the steps of:

a. administering to said human said composition comprising said IMPDH inhibitor and said alpha-interferon;

b. determining average plasma concentration produced by said IMPDH inhibitor in said human ("Cavg");

c. determining trough concentration produced by said IMPDH inhibitor in said human ("Cmin");

d. calculating a ratio of Cavg/Cmin;

e. deeming said composition to be suitable for treating HCV infection if said ratio is between 1 to 10.

It is yet another object of the present invention to provide a method of producing an optimal composition for treating HCV infection in a human, wherein said optimal composition comprises alpha-interferon and an optimal amount of an IMPDH inhibitor, said method comprising the steps of:

a. administering to said human a first composition comprising a first amount of said IMPDH inhibitor and said alpha-interferon;

b. determining average plasma concentration produced by said first amount of said IMPDH inhibitor in said human ("Cavg");

c. determining trough concentration produced by said first amount of said IMPDH inhibitor in said human "Cmin");

d. calculating a ratio of said Cavg to said Cmin;

e. modifying said first amount of said IMPDH inhibitor in said first composition to produce said optimal composition wherein said ratio is between 1 to 10.

DETAILED DESCRIPTION OF THE INVENTION

According to one embodiment, the present invention provides an optimal composition for treating HCV infection in a human. An optimal composition according to the present invention comprises alpha-interferon or a derivative thereof, an IMPDH inhibitor and a pharmaceutical carrier, wherein said IMPDH inhibitor is present in said composition in an amount such that a ratio of Cavg/Cmin is between 1 to 10;

wherein:

Cavg is average steady-state plasma concentration produced by said IMPDH inhibitor in said human; and Cmin is estimated trough concentration produced by said IMPDH inhibitor in said human.

Cavg is equal to AUC/T, wherein AUC is the area under the plasma concentration-time curve during a dosing interval of time T. Cavg and Cmin are readily determined by known techniques in the art. See, e.g., Gibaldi, M. and Perrier, D., Pharmacokinetics, $2^{nd}$ Ed., Marcel Dekker, Inc. (1982); Khakoo, S. et al., Br. J. Clin. Pharmacol. 46, pp. 563–570 (1998); Glue, P., Sem. Liver. Dis. 19, pp. 17–24 (1999).

The term "IMPDH inhibitor" as used in the present invention refers to any compound having the ability to measurably inhibit the activity of IMPDH. IMPDH inhibitors well known in the art include mycophenolic acid, ribavirin, VX-497, VX-148 or VX-944.

Thus, according to a preferred embodiment, the present invention provides an optimal composition comprising alpha-interferon or a derivative thereof, an IMPDH inhibitor and a pharmaceutical carrier, wherein said IMPDH inhibitor is present in said composition in an amount such that a ratio of Cavg/Cmin is between 1 to 10; and wherein said inhibitor is selected from mycophenolic acid, ribavirin, VX-497, VX-148 or VX-944.

According to a more preferred embodiment, the present invention provides an optimal composition comprising alpha-interferon or a derivative thereof, an IMPDH inhibitor and a pharmaceutical carrier, wherein said IMPDH inhibitor is present in said composition in an amount such that a ratio of Cavg/Cmin is between 1 to 10; and wherein said inhibitor is selected from ribavirin or VX-497.

According to an alternate more preferred embodiment, the IMPDH inhibitor is ribavirin.

According to an alternate more preferred embodiment, the IMPDH inhibitor is mycophenolic acid.

According to yet another more preferred embodiment, the IMPDH inhibitor is VX-497.

IMPDH inhibitors are known to have immunosuppressive and anti-proliferative activity by depletion of guanine nucleotide pools. Due to this anti-proliferative activity, IMPDH inhibitors such as mycophenolic acid and mizoribine are used to prevent acute graft rejection in renal and cardiac transplant patients.

However, IMPDH inhibitors are also known to have anti-viral activity. Thus, in any anti-viral therapy using IMPDH inhibitors, it is desirable to use concentrations wherein the anti-viral activity of the IMPDH inhibitor is maximized over the anti-proliferative activity. The present invention provides a band of IMPDH inhibitor concentrations, wherein the lower end of the band is defined by the ratio Cavg/Cmin being 1, and the upper end of the band is defined by that ratio being 10.

Without wishing to be bound by theory, applicants believe that the following analysis underpins the anti-viral activity of the IMPDH inhibitor:

Each IMPDH inhibitor has different IC50 values for its anti-proliferative activity ("$IC50_{ap}$") and its anti-viral activity ("$IC50_{av}$"). The ratio of $IC50_{av}/IC50_{ap}$ is the Conversion Factor ("CV"), useful in converting an anti-proliferative response into an anti-viral response.

The anti-proliferative quotient ("APQ") for a given IMPDH inhibitor, i.e., the relative-fold above $IC50_{ap}$ value of Cavg is defined as:

$$APQ = Cavg/IC50_{ap}$$

The APQ can be converted to the corresponding anti-viral quotient ("AAQ") for a given IMPDH inhibitor using the Conversion Factor described above:

$$AAQ = APQ/CV$$
$$= (Cavg/IC50_{ap})/(IC50_{av}/IC50_{ap})$$
$$= Cavg/IC50_{av}$$

The anti-viral activity is affected, in part, by the trough concentration of the IMPDH inhibitor (Cmin). Thus, the ratio $Cmin/IC50_{av}$ is defined as the Forgiveness Quotient ("FQ") and represents the relative-fold above $IC50_{av}$ value of Cmin.

Thus, for each IMPDH inhibitor, there exists an Anti-viral Index ("AI"), defined as:

$$AI = AAQ/FQ$$
$$= (Cavg/IC50_{av})/(Cmin/IC50_{av})$$
$$= Cavg/Cmin$$

Applicants believe that when AI, i.e., the ratio of Cavg/Cmin, is greater than 10, this implies that either Cavg is too high or Cmin is too low. In either event, the anti-proliferative response will tend to mask the anti-viral response, resulting in a sub-optimal level of observed anti-viral activity.

According to a preferred embodiment, the ratio of Cavg/Cmin is between 3–8.

According to a more preferred embodiment, the ratio of Cavg/Cmin is between 5–8.

According to another preferred embodiment, the ratio of Cavg/Cmin is between 1–5.

According to another more preferred embodiment, the ratio of Cavg/Cmin is between 4–6.

According to another embodiment, the present invention provides a method for treating HCV infection in a human comprising the step of administering to said human an optimal composition, wherein said optimal composition is as described above.

According to a preferred embodiment, a single dosage of the optimal composition is employed in the method of treating HCV infection according to the present invention.

According to another preferred embodiment, a multiple dosage regimen is employed for administering the optimal composition in the method of treating HCV infection according to the present invention.

According to another embodiment, the present invention provides a method for evaluating the suitability of a composition comprising an IMPDH inhibitor and alpha-interferon or a derivative thereof for treating HCV infection in a human, said method comprising the steps of:

a. administering to said human said composition comprising said IMPDH inhibitor and said alpha-interferon;

b. determining average plasma concentration produced by said IMPDH inhibitor in said human ("Cavg");

c. determining trough concentration produced by said IMPDH inhibitor in said human ("Cmin");

d. calculating a ratio of Cavg/Cmin;

e. deeming said composition to be suitable for treating HCV infection if said ratio is between 1 to 10.

According to another embodiment, the present invention provides a method of producing an optimal composition for treating HCV infection in a human, wherein said optimal composition is as defined above. The method comprises the steps of:

a. administering to said human a first composition comprising a first amount of said IMPDH inhibitor and said alpha-interferon;

b. determining average plasma concentration produced by said first amount of said IMPDH inhibitor in said human ("Cavg");

c. determining trough concentration produced by said first amount of said IMPDH inhibitor in said human ("Cmin");

d. calculating a ratio of said Cavg to said Cmin;

e. modifying said first amount of said IMPDH inhibitor in said first composition to produce said optimal composition wherein said ratio is between 1 to 10.

According to a preferred embodiment of the present invention, the ratio of Cavg/Cmin is between 1–8.

According to a more preferred embodiment of the present invention, the ratio of Cavg/Cmin is between 3–8.

According to a more preferred embodiment of the present invention, the ratio of Cavg/Cmin is between 5–8.

Pharmaceutically acceptable carriers that may be used in the optimal compositions of the present invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Such optimal pharmaceutical compositions of the present invention may be administered orally, parenterally, by inhalation spray, rectally, nasally, buccally, vaginally or via an implanted reservoir. The term "parenteral", as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, subcutaneously or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The optimal compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the optimal compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The optimal compositions of this invention may also be administered by nasal aerosol or inhalation. Such optimal compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are optimal compositions formulated for oral administration.

In order that this invention be more fully understood, the following examples are set forth. These examples are for the purpose of illustration only, and are not to be construed as limiting the scope of the invention in any way.

EXAMPLE 1

The combination therapy of interferon alpha (IFN) and ribavirin (RBV) adopted and evaluated the administration of maximum tolerated doses of both drugs (3 million units (MU) IFN three times a week (tiw)+600 mg RBV twice daily (BID)). Since the effects of IFN are indirect, a clear relationship between plasma concentration and antiviral effects has not been established. It is believed that the effects of RBV in the combination regimen ensure prevention of relapse amongst responders to IFN therapy. The latter hypothesis has been supported by higher proportion of patients having longer-term viral clearance (HCV RNA negative) following cessation of therapy, which is referred to as the sustained response (SR) rates. McHutchison and Poynard, $Sem.$ $Liver$ $Dis.$ 19, 57–65 (1999), have shown that in two major phase III trials, SR in genotype 1 and non-genotype 1 patients averaged around 30 and 60%, respectively. However, the MTD of ribavirin causes significant hemolytic anemia and various trials have indicated that dropping the ribavirin dose by one-half (to 600 mg daily) caused no significant change in SR. See, McHutchison & Poynard, $Sem.$ $Liver$ $Dis.$ 19:57–65 (1999).

As shown in Table 2a below, the FQ for RBV at any of the doses listed is well below 1 at any of the doses studied, while achieving significant antiviral effects. This surprising result indicates that the combination of IFN with IMPDH inhibitors requires a low FQ.

Our algorithm predicts that there exists an optimal balance between the antiproliferative activity and the antiviral activity for ribavirin in combination with IFN. For instance, the average trough concentrations of ribavirin are about 3.6- to 19.5-fold above the IC50 for inhibition of proliferation of peripheral blood lymphocytes (PBLs). Per our algorithm described above, a "conversion factor" of 12.25 needs to be applied to the APQ to account for antiviral effects as distinct from the antiproliferative effects of ribavirin. Thus the corrected APQ (i.e. AAQ) for ribavirin ranges from 0.3 to 1.6.

The AI for ribavirin ranges between 5 to 8 across the three doses studied. Hence, an optimal dose of ribavirin is such that its average concentration is near its concentration required for IMPDH inhibition in cell proliferation and the trough concentration is such that it allows for no greater than 10-fold ratio between APQ and FQ. Thus daily doses of 200 mg twice daily or 400 mg once daily, up to 600 mg twice daily would be effective as an IMPDH inhibitor for the inhibition of hepatitis C virus replication in combination with IFN.

TABLE 1

Effects of Interferon alpha 2b (Intron A) and Ribavirin in HCV patients

| Dose of Ribavirin | IC50ap (ng/mL) | IC50av (ng/mL)* | Cavg (ng/ml) | Cmin (ng/mL) | APQ | AAQ | FQ | HCV RNA drop |
|---|---|---|---|---|---|---|---|---|
| 600 mg BID | 976 | 11956 | 19000 | 2250 | 19.5 | 1.6 | 0.19 | 30%[a], 60%[b] |
| 400 mg BID | 976 | 11956 | 7083 | 1450 | 7.3 | 0.6 | 0.12 | N/A |
| 200 mg BID | 976 | 11956 | 3542 | 740 | 3.6 | 0.3 | 0.06 | N/A |

*Micromolar IC50 of ribavirin in Table 1 converted to ng/mL using a molecular weight of 244.
**Estimated per the single dose kinetics reported by Glue, P, Sem. Liver Dis. 19: 17–24, and using the accumulation factor reported by Khakoo et al. Br. J. Clin. Pharmacol., 46, pp. 563–570 (1998). Cavg is calculated from AUC(0 − t)/dosing interval.
†Data for SR from McHutchison and Poynard (1999), see above.
[a]For genotype 1;
[b]For non-genotype 1.
N/A: Not available

EXAMPLE 2

A four week safety and pharmacokinetic study was conducted in naive hepatitis C patients to evaluate the pharmacodynamic effects of two dose levels of VX-497 (100 mg q 8 hrs and 300 mg q 8 hrs) in combination with 3 MU of IFN alpha 2b tiw. The evaluation of the antiviral activity (with baseline HCV RNA as a covariate) of VX-497 showed that 100 mg TID produced a higher reduction in viral load than the 300 mg TID dose level. As seen in Table 2b, a lower FQ for VX-497 with the standard dose of IFN produced a similar or slightly better initial antiviral effect. Given the lower FQ for RBV in table 2 above, once again a surprising result of lower FQ giving better antiviral effects is seen.

The AAQ for VX-497's antiviral response is estimated to range between 1 and 8. When the AI is calculated, a range from 1.4 to 4.4 are obtained across all the doses for the AI. As per our algorithm, VX-497 dose levels of 50 mg BID up to 100 mg BID are also expected to elicit similar or better antiviral effects in combination with IFN as those seen in the initial antiviral study at 100 mg TID and 300 mg TID. Thus, an AI of 1–5 is considered optimal for VX-497+IFN for inhibition of hepatitis C viral replication.

significant antiviral effects, when compared to a group receiving Pegasys and RBV. However, when treated for six months with Pegasys and CellCept, similar "end of treatment" antiviral efficacy was observed for MMF and Pegasys as the combination of ribavirin and Pegasys.

Once again, the AAQ for MMF is critical in determining the activity of MMF in combination with Pegasys in hepatitis C patients. It is quite evident that the AAQ for all three dose levels of mycophenolate are well below 1. It is important to understand that in vitro inhibitory concentrations of MMF have not been predictive of in vivo EC50 for MMF. Numerous reasons for this phenomenon include rapid glucuronidation, and enterohepatic recirculation. Hence, a correction for APQ is obtained by dividing average plasma concentration by in vivo IC50.

In the case of mycophenolate, there is clear evidence of in vivo IMPDH inhibition requiring much higher concentrations. Therefore, the FQ is corrected for the loss of in vitro potency (a factor of 337.5). The AI is obtained by correcting the APQ for the fold change between antiproliferative to antiviral IC50 in vitro and an AI is obtained from the algorithm described. For mycophenolate, all three dose levels listed produce a ratio in the range of 1.9 to 2.5.

TABLE 2

Effects of Interferon alpha 2b (Intron A) and VX-497 in naïve HCV patients

| Dose of VX-497 | IC50ap (ng/mL) | IC50av* (ng/mL) | Cavg** (ng/ml) | Cmin** (ng/mL) | APQ | AAQ | FQ | % HCV RNA drop |
|---|---|---|---|---|---|---|---|---|
| 300 mg TID | 45 | 140 | 1107 | 250 | 24.6 | 7.93 | 1.8 | 50% |
| 100 mg TID | 45 | 140 | 520 | 168 | 11.6 | 3.74 | 1.2 | 53% |
| 100 mg BID | 45 | 140 | 359 | 262 | 8 | 2.6 | 1.9 | N/A |
| 50 mg TID | 45 | 140 | 266 | 116 | 5.9 | 1.9 | 0.83 | N/A |
| 50 mg BID | 45 | 140 | 150 | 107 | 3.3 | 1.06 | 0.76 | N/A |

*Micromolar IC50 in Table 1 converted to ng/mL using the molecular weight of VX-497 as 452.
**Estimated assuming linearity and based upon expected steady-state concentrations and Cavg = AUC(0 − t)/dosing interval
***From VX-497-003 trial in genotype 1 naïve patients receiving Intron-A with VX-497 for 4 weeks
N/A: Not available

EXAMPLE 3

A four-week analysis of the antiviral effects of the combination of pegylated IFN-2a (Pegasys) with the MTD of mycophenolate (as the mofetil ester, CellCept at 1000 mg BID) showed a lower proportion of patients achieving Hence, it is expected that mycophenolate at doses of 0.5 g to 1 g twice daily in combination with IFN and/or its pharmaceutical dosage forms (such as PegIntron and Pegasys), will elicit an antiviral response in hepatitis C patients.

TABLE 3

Effects of Mycophenolate with pegylated IFN-2a (Pegasys) in HCV patients

| Dose of MPA | IC50ap (ng/mL) in vitro | IC50ap** (ng/mL) in vivo | IC50av* (ng/mL) | Cavg*** (ng/mL) | Cmin** (ng/mL) | APQ | AAQ | FQ | % HCV RNA drop |
|---|---|---|---|---|---|---|---|---|---|
| 1000 mg BID | 32 | 10800 | 122 | 3869 | 2060 | 0.36 | 0.095 | 0.05 | 31[a], 72[b] |
| 750 mg BID | 32 | 10800 | 122 | 3425 | 1400 | 0.32 | 0.084 | 0.034 | N/A |
| 500 mg BID | 32 | 10800 | 122 | 3163 | 1630 | 0.29 | 0.076 | 0.04 | N/A |

Micromolar IC50 of mycophenolate in Table 1 converted to ng/mL using a molecular weight of 320.
**Estimated from Brunet et al., Transpl Int 2000; 13 (Suppl 1): S301–S305
***Cavg obtained from median AUC(0-t)/dosing interval from Brunet et al., Transpl. Int., 13, pp. 301–305 (2000)
†In vivo IMPDH inhibition correction factor estimated as the ratio of in vivo IC50/in vitro IC50 for cellular proliferation (i.e. 10800/32 = 337.5)
††Data from Nezam Afdel and Steven K. Herrine (presented at DDW, 6/2001)
[a]For non-responders to Rebetron with 90% genotype 1 patients
[b]For relapsers on Rebetron with 79% genotype 1 patients
N/A: Not available

What is claimed is:

1. A composition for treating HCV infection in a human, comprising alpha-interferon or pegylated alpha-interferon and an IMPDH inhibitor which is VX-148, wherein said IMPDH inhibitor is present in said composition in an amount such that a ratio of Cavg/Cmin is between 1 to 10; wherein:

Cavg is average plasma concentration produced by said IMPDH inhibitor in said human;
   and Cmin is estimated trough concentration produced by said IMPDH inhibitor in said human.

2. A method for treating HCV infection in a human, comprising the step of administering to said human a composition comprising alpha-interferon or pegylated alpha-interferon and an IMPDH inhibitor which is VX-148, wherein said composition comprises said IMPDH inhibitor in an amount such that a ratio of Cavg/Cmin is between 1 to 10:
wherein:

Cavg is average plasma concentration produced by said IMPDH inhibitor in said human;
   and Cmin is estimated trough concentration produced by said IMPDH inhibitor in said human.

3. A method for evaluating the suitability of a composition comprising an IMPDH inhibitor and alpha-interferon or pegylated alpha-interferon for treating HCV infection in a human, said method comprising the steps of:

a. administering to said human said composition comprising said IMPDH inhibitor and said alpha-interferon or said pegylated alpha-interferon;
   b. determining average plasma concentration produced by said IMPDH inhibitor in said human ("Cavg");
   c. determining trough concentration produced by said IMPDH inhibitor in said human ("Cmin");
   d. calculating a ratio of Cavg/Cmin;
   e. deeming said composition to be suitable for treating HCV infection if said ratio is between 1 to 10.

4. A method of producing an optimal composition for treating HCV infection in a human, said method comprising the steps of:

a. administering to a human a first composition comprising a first amount of VX-148 and alpha-interferon or pegylated alpha-interferon;
   b. determining average plasma concentration produced by said first amount of said VX-148 in said human ("Cavg");
   c. determining trough concentration produced by said first amount of said VX-148 in said human ("Cmin");
   d. calculating a ratio of said Cavg to said Cmin;
   e. modifying said first amount of said VX-148 in said first composition to a second amount of said VX-148 such that said ratio is between 1 to 10; and
   f. combining said second amount of said VX-148 with said alpha-interferon or said pegylated alpha-interferon to produce said optimal composition.

5. The method according to any of claims 2–4, wherein said ratio is between 1–8.

6. The method according to claim 5, wherein said ratio is between 3–8.

7. The method according to claim 6, wherein said ratio is between 5–8.

* * * * *